United States Patent
Nebuya

(10) Patent No.: US 10,330,620 B2
(45) Date of Patent: Jun. 25, 2019

(54) DETECTION DEVICE, DETECTION SYSTEM, DETECTION METHOD, AND PROGRAM

(71) Applicant: SCHOOL JURIDICAL PERSON KITASATO INSTITUTE, Tokyo (JP)

(72) Inventor: Satoru Nebuya, Sagamihara (JP)

(73) Assignee: SCHOOL JURIDICAL PERSON KITASATO INSTITUTE, Tokyo (JP)

(*) Notice: Subject to any disclaimer, the term of this patent is extended or adjusted under 35 U.S.C. 154(b) by 292 days.

(21) Appl. No.: 15/302,247

(22) PCT Filed: Apr. 7, 2015

(86) PCT No.: PCT/JP2015/060821
§ 371 (c)(1),
(2) Date: Dec. 23, 2016

(87) PCT Pub. No.: WO2015/156277
PCT Pub. Date: Oct. 15, 2015

(65) Prior Publication Data
US 2017/0199143 A1 Jul. 13, 2017

(30) Foreign Application Priority Data

Apr. 7, 2014 (JP) ................. 2014-078997

(51) Int. Cl.
*G01R 19/00* (2006.01)
*G01N 27/06* (2006.01)
(Continued)

(52) U.S. Cl.
CPC ......... *G01N 27/06* (2013.01); *A61B 5/02042* (2013.01); *A61F 13/42* (2013.01);
(Continued)

(58) Field of Classification Search
USPC ....... 324/694, 71.1, 715, 717; 600/327, 345, 600/587
See application file for complete search history.

(56) References Cited

U.S. PATENT DOCUMENTS 5,579,765 A 12/1996 Cox et al.
2002/0137999 A1 9/2002 Bandeian, Jr. et al.
(Continued)

FOREIGN PATENT DOCUMENTS

DE 10 2012 011 212 12/2012
JP 52-110887 8/1977
(Continued)

OTHER PUBLICATIONS

International Search Resort issued in PCT/JP2015/060821 dated May 19, 2015.
(Continued)

*Primary Examiner* — Vincent Q Nguyen
(74) *Attorney, Agent, or Firm* — Nixon & Vanderhye P.C.

(57) ABSTRACT

A detection device includes: a frequency property acquisition unit that acquires a frequency property when an alternating-current signal is input to at least two conductive bodies provided on a fiber sheet; and a detection signal output unit that outputs a detection signal when the frequency property acquisition unit acquires a predetermined frequency property.

10 Claims, 13 Drawing Sheets

(51) Int. Cl.
*A61M 1/14* (2006.01)
*G01N 33/487* (2006.01)
*G01R 23/00* (2006.01)
*A61B 5/02* (2006.01)
*A61F 13/42* (2006.01)
*D02G 3/44* (2006.01)
*A61B 5/00* (2006.01)
*A61B 5/053* (2006.01)
*A61B 5/145* (2006.01)

(52) U.S. Cl.
CPC ............... *A61M 1/14* (2013.01); *D02G 3/441* (2013.01); *G01N 33/48785* (2013.01); *G01R 23/005* (2013.01); *A61B 5/0531* (2013.01); *A61B 5/14517* (2013.01); *A61B 5/6892* (2013.01); *A61B 2562/029* (2013.01); *A61B 2562/0209* (2013.01); *A61F 2013/424* (2013.01); *A61M 2205/13* (2013.01); *A61M 2205/18* (2013.01); *A61M 2205/581* (2013.01); *A61M 2205/583* (2013.01); *D10B 2403/02431* (2013.01); *D10B 2509/00* (2013.01)

(56) References Cited

U.S. PATENT DOCUMENTS

| | | | | |
|---|---|---|---|---|
| 2005/0070861 | A1* | 3/2005 | Okabe | A61F 5/4404 604/327 |
| 2006/0122540 | A1* | 6/2006 | Zhu | A61B 5/0537 600/587 |
| 2010/0076283 | A1* | 3/2010 | Simpson | A61B 5/14532 600/345 |
| 2011/0132040 | A1 | 6/2011 | Jahn et al. | |
| 2012/0029410 | A1 | 2/2012 | Koenig et al. | |

FOREIGN PATENT DOCUMENTS

| | | |
|---|---|---|
| JP | 60-181311 | 12/1985 |
| JP | 61-56568 | 4/1986 |
| JP | 62-139519 | 9/1987 |
| JP | 2-174846 | 7/1990 |
| JP | 11-347058 | 12/1999 |
| JP | 3552997 | 8/2004 |
| JP | 2005-73974 | 3/2005 |
| JP | 2005-516637 | 6/2005 |
| JP | 2006-110119 | 4/2006 |
| JP | 2007-151624 | 6/2007 |
| JP | 2007-159736 | 6/2007 |
| JP | 2007-248409 | 9/2007 |
| JP | 2009-528519 | 8/2009 |
| JP | 4638391 | 2/2011 |
| JP | 2011-75529 | 4/2011 |
| JP | 2011-106084 | 6/2011 |
| JP | 2012-517832 | 8/2012 |
| JP | 2012-196293 | 10/2012 |
| JP | 2014-151096 | 8/2014 |
| JP | 2014-185924 | 10/2014 |
| WO | WO 03/000315 | 1/2003 |
| WO | WO 2005/099644 | 10/2005 |
| WO | WO 2007/098762 | 9/2007 |
| WO | WO 2008/104397 | 9/2008 |
| WO | WO 2011/004165 | 1/2011 |
| WO | WO 2013/169667 | 11/2013 |

OTHER PUBLICATIONS

Japanese Office Action issued in App. No. 2014-078997 dated Nov. 24, 2014 (w/ translation).
Jasanese Office Action issued in App. No. 2014-078997 dated Mar. 24, 2015 (w/ translation).
Extended European Search Resort issued in Appln. No. 15776844.1 dated Nov. 24, 2017.

* cited by examiner

DETECTION DEVICE, DETECTION SYSTEM, DETECTION METHOD, AND PROGRAM

This application is the U.S. national phase of International Application No. PCT/JP2015/060821 filed 7 Apr. 2015 which designated the U.S. and claims priority to JP Patent Application No. 2014-078997 filed 7 Apr. 2014, the entire contents of each of which are hereby incorporated by reference.

TECHNICAL FIELD

The present invention relates to a detection device, a detection system, a detection method, and a program.

Priority is claimed on Japanese Patent Application No. 2014-078997 filed on Apr. 7, 2014, the contents of which are incorporated herein by reference.

BACKGROUND

Needle removal at the time of artificial dialysis may lead to a serious accident due to sudden bleeding, and therefore, prompt detection is required when needle removal occurs. Therefore, as one of detection methods of needle removal, a method has been proposed in which needle removal is detected by detecting bleeding. In the method, in order to prevent erroneous detection, it is desired to detect blood such that blood is distinguished from sweat. In this way, there may be a case in which it is required to detect adherence to a sensor of specific fluid such that the adherence of the specific fluid is distinguished from adherence to the sensor of another fluid.

In association with the detection of needle removal at the time of artificial dialysis, in an artificial dialysis blood detection device described in Patent Document 1, a water sensor includes an electrode sheet, a filter sheet, and a water permeable sheet. The electrode sheet includes a base sheet having a three layer structure and a reinforcement sheet. The reinforcement sheet has a large number of microscopic holes and not only includes air permeability that allows water vapor to pass through the reinforcement sheet but also includes a waterproof property that prevents water droplets from passing through the reinforcement sheet. A connector includes a lever and a clip. Each of the lever and the clip clips one end part and the other end part of the water sensor. The clip includes a normally-closed switch. When the clip holds the water sensor, the switch switches to an OFF state. When the clip is removed from the water sensor, the switch switches to an ON state.

Patent Document 1 states that thereby, it is possible to reliably detect a probability of needle removal and bleeding due to needle removal without causing an erroneous operation due to sweat.

RELATED ART DOCUMENTS

Patent Documents

[Patent Document 1] Japanese Patent Application, Publication No. 2012-196293

SUMMARY OF INVENTION

Technical Problem

In the artificial dialysis blood detection device described in Patent Document 1, the water sensor to which blood adheres at the time of bleeding has a complicated structure as described above. Therefore, a great amount of money is required to produce the water sensor, and there is a possibility in that the water sensor cannot be disposable. On the other hand, from a viewpoint of further reliably preventing blood infection of diseases, a part to which blood may adhere is preferably disposable.

In this way, there may be a case in which it is desirable that adherence of specific fluid such as blood can be detected such that the specific fluid is distinguished from another fluid such as sweat and it is desirable that a part to which the fluid adheres can be disposable.

An object of an aspect of the present invention is to provide a detection device, a detection system, a detection method, and a program in which adherence of specific fluid can be detected such that the specific fluid is distinguished from another fluid, and a part to which the fluid adheres can be disposed of.

Solution to Problem

According to a first aspect of the present invention, a detection device includes: a frequency property acquisition unit that acquires a frequency property when an alternating-current signal is input to at least two conductive bodies provided on a fiber sheet; and a detection signal output unit that outputs a detection signal when the frequency property acquisition unit acquires at least one of a frequency property that indicates a predetermined difference according to a frequency difference between the alternating-current signals input to the conductive bodies and a frequency property that indicates a predetermined change according to a time elapse.

The frequency property acquisition unit may acquire a frequency property when each of an alternating-current signal in a first frequency and an alternating-current signal in a second frequency is input to the at least two conductive bodies, and the detection signal output unit may output the detection signal when a difference between a frequency property when the alternating-current signal in the first frequency is input to the conductive bodies and a frequency property when the alternating-current signal in the second frequency is input to the conductive bodies is a predetermined difference.

According to a second aspect of the present invention, a detection system includes: a fiber sheet; and a detection device, wherein at least two conductive bodies are provided on the fiber sheet, and the detection device includes: a frequency property acquisition unit that acquires a frequency property when an alternating-current signal is input to at least two conductive bodies provided on the fiber sheet; and a detection signal output unit that outputs a detection signal when the frequency property acquisition unit acquires at least one of a frequency property that indicates a predetermined difference according to a frequency difference between the alternating-current signals input to the conductive bodies and a frequency property that indicates a predetermined change according to a time elapse.

The fiber sheet may include a thread including at least two conductive bodies which are combined such that the conductive bodies do not come into contact with each other.

The thread may include a first conductive body, an insulation material having a water absorption property, and a second conductive body, and the first conductive body may be covered by the insulation material having a water absorption property and be further winded by the second conductive body.

The two conductive bodies may be twisted together such that the conductive bodies do not come into contact with each other.

According to a third aspect of the present invention, a detection method is a detection method of a detection device, the detection method including: a frequency property acquisition step of, by way of the detection device, acquiring a frequency property when an alternating-current signal is input to at least two conductive bodies provided on a fiber sheet; and a detection signal output step of, by the detection device, outputting a detection signal when in the frequency property acquisition step, at least one of a frequency property that indicates a predetermined difference according to a frequency difference between the alternating-current signals input to the conductive bodies and a frequency property that indicates a predetermined change according to a time elapse is acquired.

According to a fourth aspect of the present invention, a program is a program that causes a computer to execute a detection signal output step of outputting a detection signal when, with respect to a frequency property when an alternating-current signal is input to at least two conductive bodies provided on a fiber sheet, at least one of a frequency property that indicates a predetermined difference according to a frequency difference between the alternating-current signals input to the conductive bodies and a frequency property that indicates a predetermined change according to a time elapse is acquired.

Advantage of the Invention

According to the aspect of the present invention, adherence of specific fluid can be detected such that the specific fluid is distinguished from another fluid, and a part to which the fluid adheres can be disposable.

DESCRIPTION OF EMBODIMENTS

Hereinafter, an embodiment of the present invention is described. The following embodiment does not limit the invention according to claims. All combinations of features described in the embodiment are not necessarily required for means for solving the problem of the invention.

Figure 1:
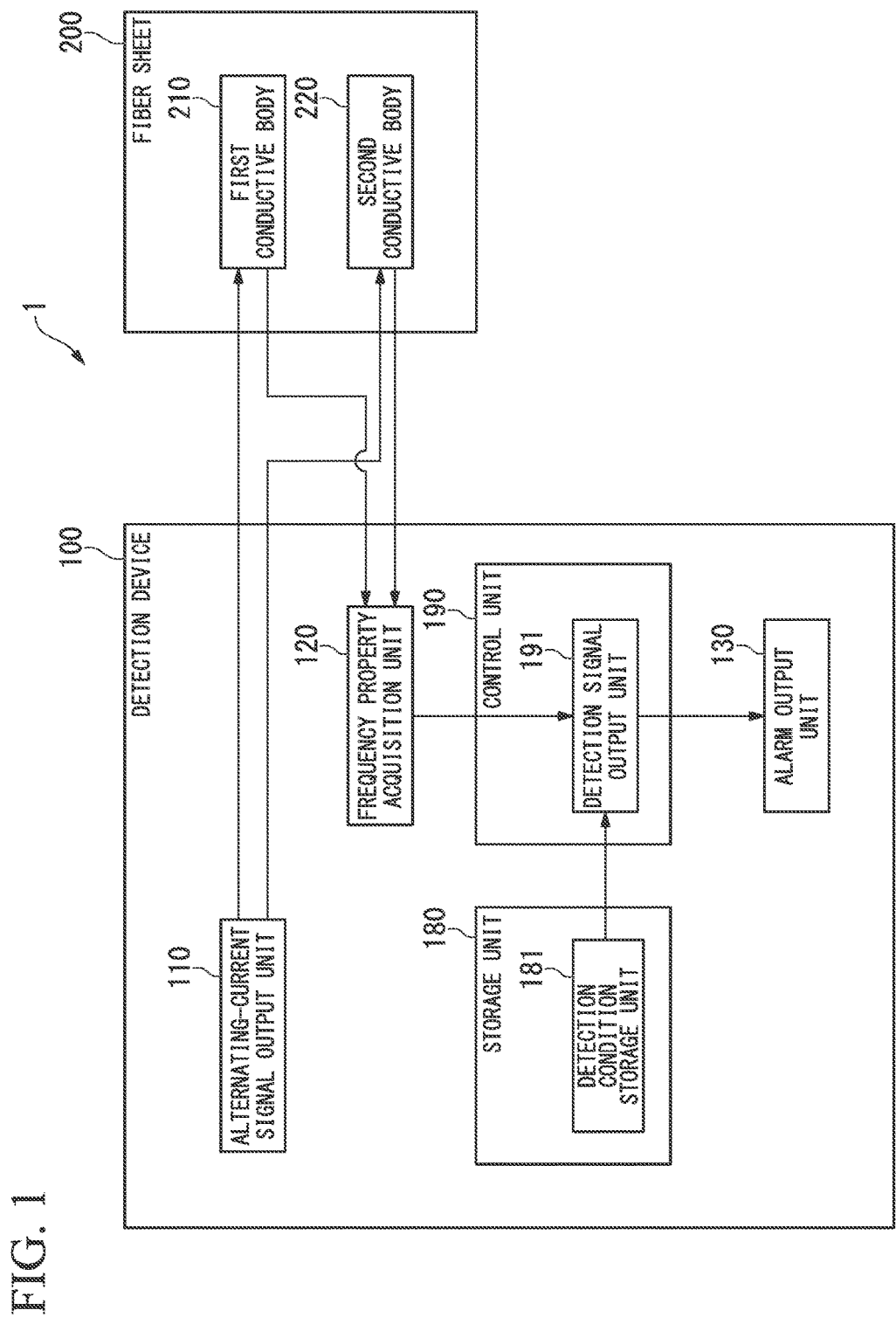
FIG. 1 is a schematic block diagram showing a functional configuration of a frequency property detection system in an embodiment of the present invention.

FIG. 1 is a schematic block diagram showing a functional configuration of a frequency property detection system in an embodiment of the present invention. In FIG. 1, a detection system 1 includes a detection device 100 and a fiber sheet 200. The detection device 100 includes an alternating-current signal output unit 110, a frequency property acquisition unit 120, an alarm output unit 130, a storage unit 180, and a control unit 190. The storage unit 180 includes a detection condition storage unit 181. The control unit 190 includes a detection signal output unit 191. The fiber sheet 200 includes a first conductive body 210 and a second conductive body 220. As described below, the detection signal output unit 191 is configured to output a detection signal when a frequency property acquisition unit 120 acquires at least one of (a) a frequency property that indicates a predetermined difference according to a frequency difference between alternating-current signals input to a conductive body and (b) a frequency property that indicates a predetermined change according to a time elapse.

The detection system 1 detects needle removal by detecting the leakage of blood at the time of artificial dialysis.

Figure 2:
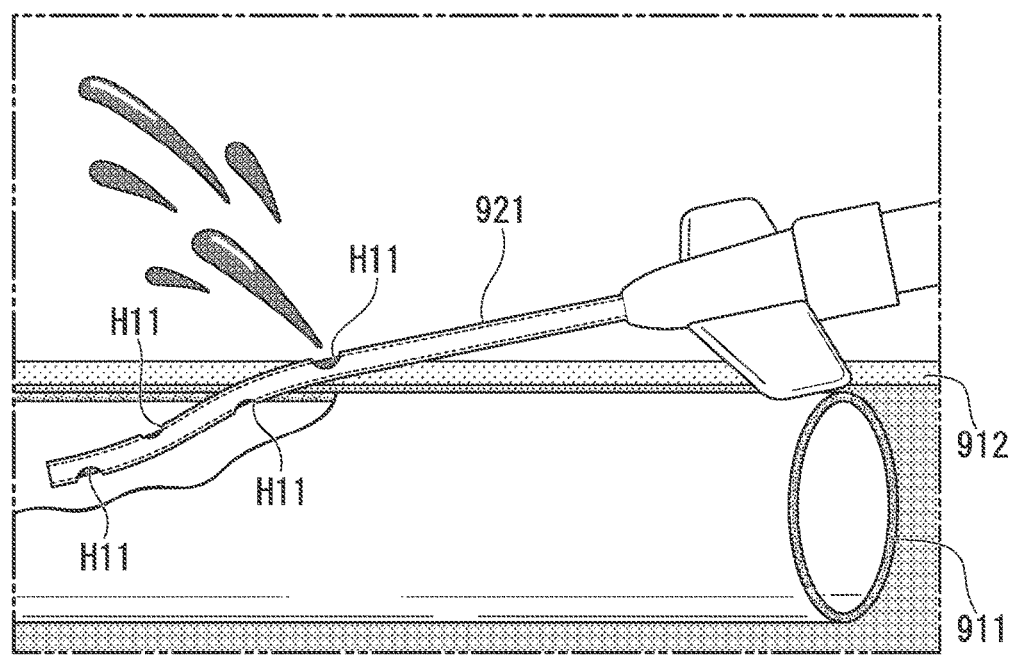
FIG. 2 is an explanatory diagram showing an example of needle removal in artificial dialysis.

FIG. 2 is an explanatory diagram showing an example of needle removal in artificial dialysis. In FIG. 2, a teflon needle (teflon is a registered trademark) 921 is inserted in a blood vessel 911, and a lateral groove H11 is provided on the teflon needle 921. When blood is taken from a body to an artificial dialysis device, the teflon needle 921 is inserted in an artery. When blood is returned from the artificial dialysis device to the body, the teflon needle 921 is inserted in a vein.

In the example of FIG. 2, part of the teflon needle 921 is removed out of the body (out of a skin 912), and blood is leaking from the lateral groove H11 exposed outside the body.

In particular, when blood is returned, due to the impact of increasing the pressure of blood at the artificial dialysis device, needle removal occurs more easily than when blood is taken. Further, when artificial dialysis is repeated or the blood vessel is weak due to the impact of diabetes or the like, needle removal easily occurs.

The fiber sheet 200 is laid under an arm to which a needle is tapped in artificial dialysis. For example, during artificial dialysis, a patient lies on a bed and receives dialysis. The fiber sheet 200 is laid on the bed, and the teflon needle 921 (FIG. 2) is tapped to the arm of the patient arranged on the fiber sheet 200. The fiber sheet 200 has a water absorption property and prevents blood, sweat, or the like from leaking to the bed. The fiber sheet 200 may have a waterproof property in addition to or in place of the water absorption property. Thereby, it is possible to further reliably prevent blood, sweat, or the like from leaking to the bed.

The fiber sheet 200 may be formed as a bandage or gauze. For example, the fiber sheet 200 formed as a bandage can be used, for example, by winding the fiber sheet 200 around a blood leakage monitor target part such as an arm to which a needle is tapped during artificial dialysis. Further, the fiber sheet 200 formed as gauze can be used by applying the fiber sheet 200 to the blood leakage monitor target part and winding the fiber sheet 200 by a bandage.

When a patient moves widely, for example, when the patient turns over in bed, according to a method in which the fiber sheet 200 is laid on the bed and the arm of the patient is provided on the fiber sheet 200, there is a possibility in that blood leaks outside the fiber sheet 200 depending on the size of the fiber sheet 200.

On the other hand, the fiber sheet 200 formed as a bandage is used by winding the fiber sheet 200 around a blood leakage monitor target part, and thereby, it is possible to reduce a possibility in that the fiber sheet 200 is removed from the blood leakage monitor target part, and the leakage of blood can be further reliably detected. Similarly, the fiber sheet 200 is used by applying the fiber sheet 200 to the blood leakage monitor target part and winding the fiber sheet 200 by a bandage, and thereby, it is possible to reduce a possibility in that the fiber sheet 200 is removed from the blood leakage monitor target part, and the leakage of blood can be further reliably detected.

There is a case in which the tapped part is fixed by winding the part using a bandage, for example, when the patient may remove the needle for oneself. In this case, according to the method in which the fiber sheet 200 is laid on the bed and the arm of the patient is provided on the fiber sheet 200, there is a possibility in that the detection device 100 cannot detect the leakage of blood inside the bandage. On the other hand, the tapped part is fixed by winding the fiber sheet 200 formed as a bandage around the tapped part, and thereby, the detection device 100 can further reliably detect the leakage of blood inside the bandage. Further, the gauze or needle is fixed by applying the fiber sheet 200 formed as gauze to the tapped part and winding the fiber sheet 200 by a bandage, and thereby, the detection device 100 can further reliably detect the leakage of blood inside the bandage.

Each of the first conductive body 210 and the second conductive body 220 is a conductive body provided on the fiber sheet 200, and an alternating-current signal from the alternating-current signal output unit 110 is input to each of the first conductive body 210 and the second conductive body 220.

The first conductive body 210 and the second conductive body 220 are not in contact with each other, and a main body (a part which becomes a base on which the first conductive body 210 and the second conductive body 220 are provided) of the fiber sheet 200 is made of a fiber having an insulation property. Therefore, in a state where fluid does not adhere to the fiber sheet 200, the first conductive body 210 and the second conductive body 220 are isolated from each other, or merely a very small alternating-current flows between the first conductive body 210 and the second conductive body 220 due to a condenser effect or the like.

On the other hand, when fluid is dropped on between the first conductive body 210 and the second conductive body 220, the first conductive body 210 and the second conductive body 220 are electrically conducted to each other with a frequency property that corresponds to the dropped fluid.

When the fiber sheet 200 has a water absorption property and causes fluid to diffuse, even when fluid is dropped on a position other than a position between the first conductive body 210 and the second conductive body 220, the possibility in that the first conductive body 210 and the second conductive body 220 are electrically conducted to each other can be enhanced. Specifically, it is possible to enhance a possibility in that the detection system 1 can detect the leakage of blood.

A configuration in which the arm of the patient does not directly come into contact with the first conductive body 210 and the second conductive body 220, such as a configuration in which a layer having a water absorption property and having an insulation property is provided on the surfaces of the first conductive body 210 and the second conductive body 220, may be employed. Alternatively, the detection system 1 (detection device 100) may detect an electrical conduction property (frequency property) which is distinguishable from a contact with the arm of the patient, and thereby, the leakage of blood may be detected.

As materials of the first conductive body 210 and the second conductive body 220, a variety of materials having an electrical conductivity can be used. For example, an electrically conductive thread (thread having an electrical conductivity) may be used as the first conductive body 210 and the second conductive body 220, and the electrically conductive thread may be interwoven when the fiber sheet 200 is produced. Alternatively, an electrically conductive thread may be used as the first conductive body 210 and the second conductive body 220, and the electrically conductive thread may be sewed to the main body of the fiber sheet 200 after production.

By using the electrically conductive thread as the first conductive body 210 and the second conductive body 220, it is possible to improve textures of the fiber sheet 200. Thereby, it is possible to avoid providing a feeling of discomfort when the patient puts the arm on the fiber sheet 200.

The detection device 100 inputs an alternating-current signal to the fiber sheet 200, acquires a frequency property in the fiber sheet 200, and determines the presence or absence of the leakage of blood.

A variety of signals (that is, a variety of signals having a frequency) in which a voltage varies can be used as the alternating-current signal that the detection device 100 inputs to the fiber sheet 200. For example, the detection device 100 may input a sine wave to the fiber sheet 200, may input a triangle wave to the fiber sheet 200, or may input a rectangular wave to the fiber sheet 200.

The frequency property acquired by the detection device 100 can be a variety of data measured in accordance with the frequency of an input alternating-current signal. The present embodiment is described using an example in which the detection device 100 measures impedance or a phase rotation as the frequency property; however, the embodiment is not limited thereto.

The detection device 100 includes, for example, a microcomputer. Alternatively, a configuration other than the configuration including a microcomputer may be used such as a configuration in which each unit of the detection device 100 is formed of a dedicated circuit, or a configuration in which each unit of the detection device 100 is formed using a smartphone, a personal computer, or the like.

The alternating-current signal output unit 110 outputs an alternating-current signal to be input to the fiber sheet 200. As described above, a variety of signals in which a voltage varies can be used as the alternating-current signal output by the alternating-current signal output unit 110.

The frequency property acquisition unit 120 acquires a frequency property when the alternating-current signal output unit 110 inputs the alternating-current signal to at least two conductive bodies (in the present embodiment, to the first conductive body 210 and the second conductive body 220) provided on the fiber sheet 200. For example, the frequency property acquisition unit 120 measures the impedance of the fiber sheet 200 in the frequency of the alternating-current signal output by the alternating-current signal output unit 110 or the phase rotation of the alternating-current signal in the fiber sheet 200 with respect to the alternating-current signal output by the alternating-current signal output unit 110. Further, for example, the frequency property acquisition unit 120 measures the impedance between the first conductive body 210 and the second conductive body 220 or the phase rotation of the current flowing between the first conductive body 210 and the second conductive body 220 with respect to the alternating-current signal output by the alternating-current signal output unit 110.

Specifically, the frequency property acquisition unit 120 acquires a frequency property when each of an alternating-current signal in a first frequency and an alternating-current signal in a second frequency is input to the first conductive body 210 and the second conductive body 220. As described below, the amplitude of the change in impedance with respect to the change in a frequency or the amplitude of the change in a phase rotation differs between blood and sweat. Therefore, the frequency property acquisition unit 120 measures, with respect to each of the alternating-current signals having a different frequency, a frequency property when the alternating-current signals are input to the first conductive body 210 and the second conductive body 220.

The detection device 100 (detection signal output unit 191) detects the leakage of blood according to the frequency property with respect to each of the alternating-current signals having a different frequency, and thereby, it is possible to distinguish between blood and sweat. Thereby, it is possible to reduce erroneous detection of needle removal.

The alarm output unit 130 outputs an alarm when the detection device 100 (detection signal output unit 191) detects the leakage of blood according to the frequency property acquired by the frequency property acquisition unit 120.

A variety of methods can be used as an alarm output method of the alarm output unit 130. For example, the alarm output unit 130 includes a speaker and outputs an alarm sound in response to the detection signal output by the detection signal output unit 191. Alternatively, the alarm output unit 130 may include a lamp in addition to or in place of the speaker and output an alarm by way of light emission of the lamp. Alternatively, the alarm output unit 130 may transmit an alarm signal to another device, for example, transmit an alarm signal to a personal computer (PC) provided at a nurse center.

The storage unit 180 includes, for example, a storage device included in the detection device 100 and stores a variety of data.

The detection condition storage unit 181 stores a determination threshold value whether or not the detection signal output unit 191 outputs a detection signal. That is, the threshold value is used as a detection condition when the detection signal output unit 191 determines whether or not the leakage of blood is detected.

The control unit 190 controls each unit of the detection device 100 and performs a variety of functions. For example, a central processing unit (CPU) included in the detection device 100 reads out a program from the storage unit 180 and executes the program, and thereby the control unit 190 is realized.

When the frequency property acquisition unit 120 acquires a predetermined frequency property, the detection signal output unit 191 outputs a detection signal. More specifically, the detection signal output unit 191 determines whether or not the frequency property acquired by the frequency property acquisition unit 120 satisfies the detection condition stored by the detection condition storage unit 181. Then, when the detection signal output unit 191 determines that the detection condition is satisfied, the detection signal output unit 191 outputs the detection signal to the alarm output unit 130.

Specifically, when a difference between a frequency property when the alternating-current signal in the first frequency is input to the first conductive body 210 and the second conductive body 220 and a frequency property when the alternating-current signal in the second frequency is input to the first conductive body 210 and the second conductive body 220 is a predetermined difference, the detection signal output unit 191 outputs a detection signal. More specifically, the alternating-current signal output unit 110 inputs alternating-current powers having a different frequency (first frequency and second frequency) as described above to the fiber sheet 200. Then, the frequency property acquisition unit 120 measures impedance or a phase rotation with respect to each frequency. Then, when the detection signal output unit 191 determines that the amplitude of the change in impedance according to the change in a frequency or the amplitude of a phase rotation satisfies the detection condition stored by the detection condition storage unit 181, the detection signal output unit 191 outputs a detection signal to the alarm output unit 130.

Next, with reference to FIG. 3 to FIG. 8, a determination condition for detecting the leakage of blood by the detection signal output unit 191 is described. In an experiment, frequency properties different from each other have been obtained between swine blood that simulates human blood and salt water that simulates sweat, and according to such an experiment result, it is possible to set a determination condition for detecting the leakage of blood by the detection signal output unit 191.

Figure 3:
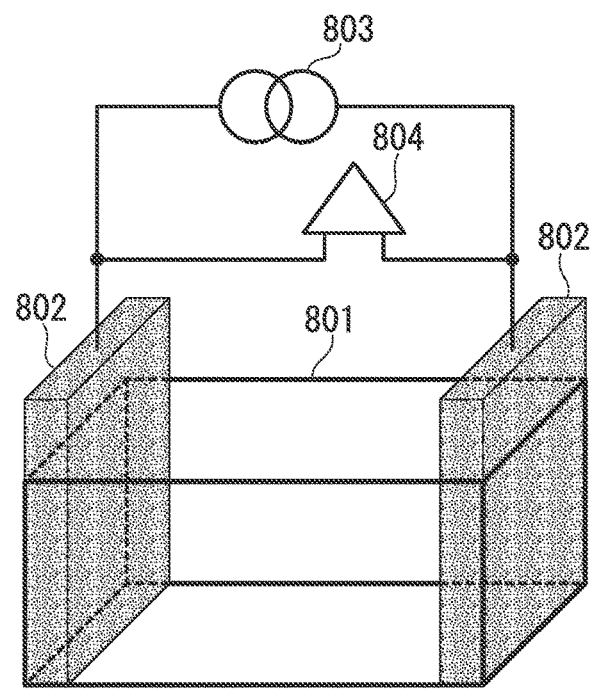
FIG. 3 is an appearance diagram showing the outline of the external form of a container and a measurement electrode used in an experiment regarding the embodiment.

FIG. 3 is an appearance diagram showing the outline of the external form of a container and a measurement electrode used in the experiment. In the experiment, one of electrodes 802 was inserted at each of ends of an acrylic container 801, and blood or salt water was put in the container. The acrylic container 801 was put in a constant temperature bath, and the experiment was performed at a temperature (37° C.) close to body temperature.

Each of the electrodes 802 was connected to an alternating-current electric source 803, and an alternating-current signal was caused to flow. Each of the electrodes 802 was connected to a voltmeter 804, and a voltage between the electrodes 802 was measured by the voltmeter 804.

The electrodes 802 simulate the first conductive body 210 and the second conductive body 220. The electric source 803 simulates the alternating-current signal output unit 110. The voltmeter 804 simulates the frequency property acquisition unit 120.

Figure 4:
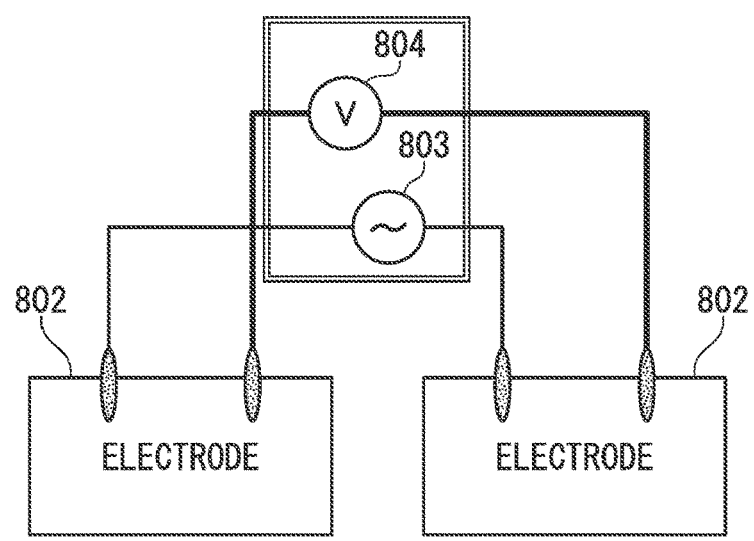
FIG. 4 is an explanatory diagram showing the outline of a circuit in the experiment regarding the embodiment.

FIG. 4 is an explanatory diagram showing the outline of a circuit in the experiment. As shown in FIG. 4, the electric source 803 is connected to and between the two electrodes 802, and an alternating-current signal is input to the two electrodes 802. The voltmeter 804 is connected to and between the two electrodes 802 and measures the voltage between the two electrodes 802.

In the experiment, blood of ten swine was used, and the average value was calculated. The hematocrit value (Hct) of the blood used in the experiment is about 40(%).

Further, sodium citrate was used as an anticoagulant for non-coagulated blood.

Figure 5:
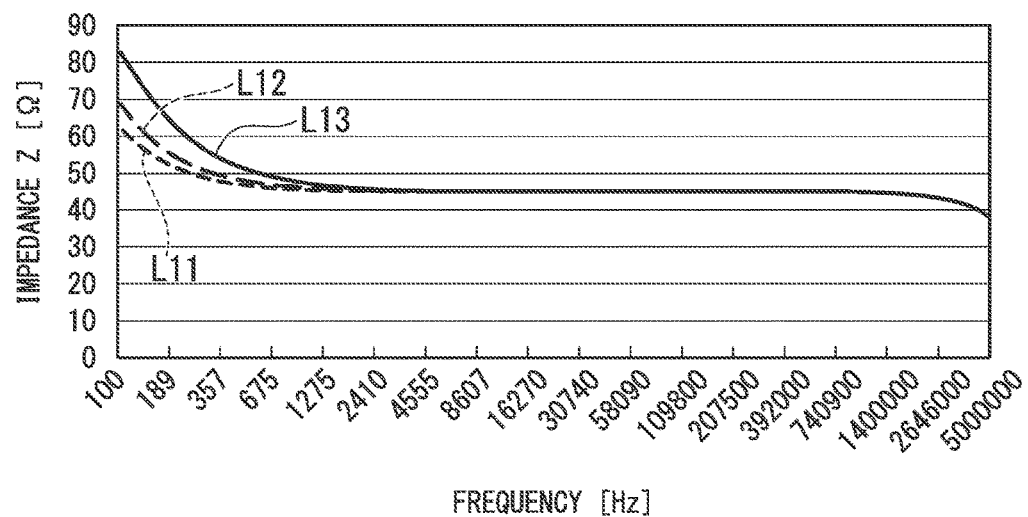
FIG. 5 is a graph showing a measurement result of an amplitude Z of impedance in a state where an acrylic container contains salt water in the experiment regarding the embodiment.

FIG. 5 is a graph showing a measurement result of an amplitude Z of impedance in a state where the acrylic container 801 contains salt water. The horizontal axis of the graph shown in FIG. 5 represents a frequency, and the vertical axis represents impedance.

In the experiment, salt water was put in three acrylic containers 801 (hereinafter, referred to as a container A, a container B, and a container C) having a different size, and the impedance was measured. The frequency property in a state where the acrylic container 801 contains salt water indicates the frequency property of the acrylic container 801 itself. The frequency property in a state where the acrylic container 801 contains salt water simulates the frequency property of sweat.

A line L11 represents an impedance measurement value for the container A, a line L12 represents an impedance measurement value for the container B, and a line L13 represents an impedance measurement value for the container C. All lines L11, L12, L13 indicate substantially constant impedance in the range of about 3 kHz to about 2 MHz.

Figure 6:
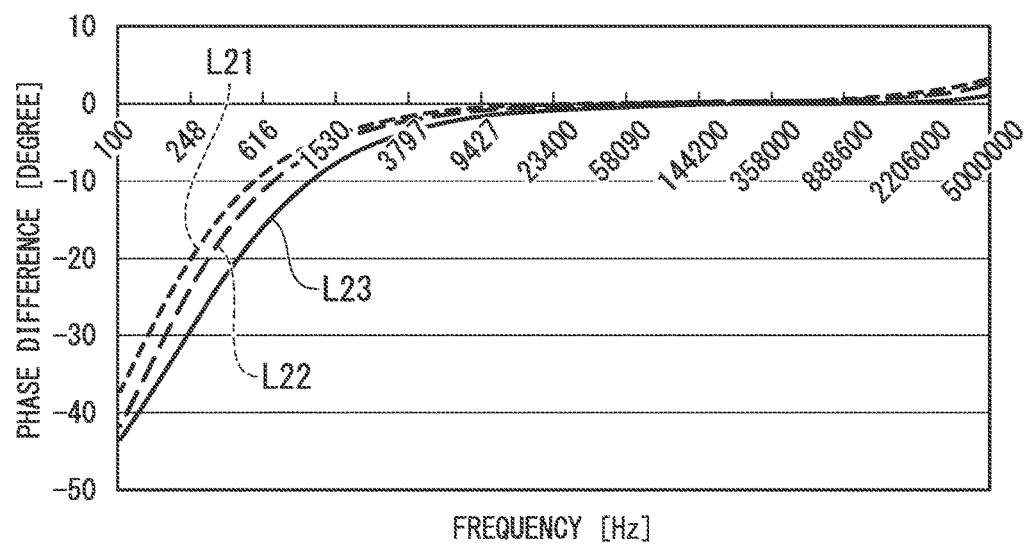
FIG. 6 is a graph showing a measurement result of a phase difference (phase rotation) in a state where the acrylic container contains salt water in the experiment regarding the embodiment.

FIG. 6 is a graph showing a measurement result of a phase difference (phase rotation) in a state where the acrylic container 801 contains salt water. The phase difference here is a difference between a phase of the alternating-current signal output by the electric source 803 and a phase of the alternating-current signal between the electrodes 802 of which the voltage is measured by the voltmeter 804.

The horizontal axis of the graph shown in FIG. 6 represents frequency, and the vertical axis represents phase difference. A line L21 represents phase difference for the container A, a line L22 represents a phase difference for the container B, and a line L23 represents a phase difference for the container C. All lines L11, L12, L13 indicate a substantially constant phase difference (substantially zero phase difference) in the range of about 40 kHz to about 2 MHz.

From the measurement results of FIG. 5 and FIG. 6, both the amplitude and the phase are substantially constant in the range of about 40 kHz to about 2 MHz in the case of salt water.

Figure 7:
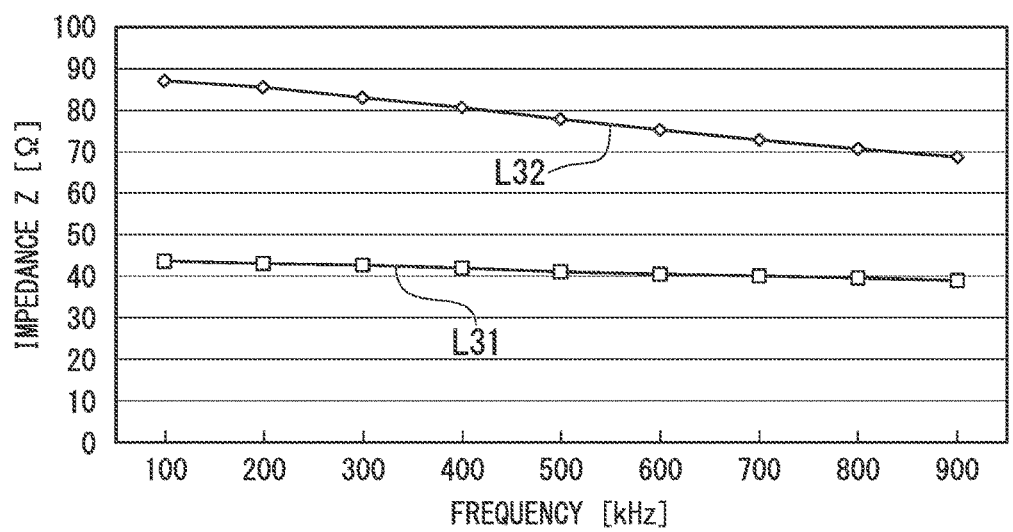
FIG. 7 is a graph showing a measurement result of an amplitude Z of impedance in a state where the acrylic container contains swine blood in the experiment regarding the embodiment.

FIG. 7 is a graph showing a measurement result of an amplitude Z of impedance in a state where the acrylic container 801 contains swine blood. The horizontal axis of the graph shown in FIG. 7 represents a frequency, and the vertical axis represents impedance. The frequency property in a state where the acrylic container 801 contains swine blood simulates the frequency property of human blood.

A line L31 represents impedance of non-coagulated blood. A line L32 represents impedance of coagulated blood.

In the case of the non-coagulated blood represented by the line L31, the impedance is decreased as the frequency is increased from 100 kHz to 900 kHz. In the case of the coagulated blood represented by the line L32, the impedance is greater than the impedance in the case of the non-coagulated blood, and the rate of the decrease of the impedance to the increase of the frequency is also greater than the rate in the case of the non-coagulated blood.

Figure 8:
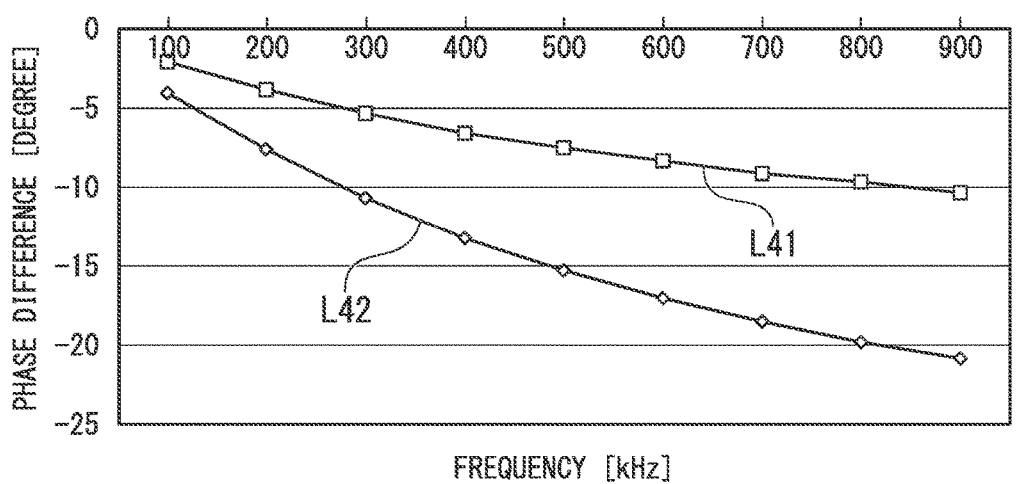
FIG. 8 is a graph showing a measurement result of a phase difference (phase rotation) in a state where the acrylic container contains swine blood in the experiment regarding the embodiment.

FIG. 8 is a graph showing a measurement result of a phase difference (phase rotation) in a state where the acrylic container 801 contains swine blood. Similarly to the case of FIG. 6, the phase difference in FIG. 8 is a difference between a phase of the alternating-current signal output by the electric source 803 and a phase of the alternating-current signal between the electrodes 802 of which the voltage is measured by the voltmeter 804. The horizontal axis of the graph shown in FIG. 8 represents a frequency, and the vertical axis represents a phase difference.

A line L41 represents a phase difference in the case of non-coagulated blood. A line L42 represents a phase difference in the case of coagulated blood.

In the case of the non-coagulated blood represented by the line L41, the phase difference (phase lag) is increased as the frequency is increased from 100 kHz to 900 kHz. In the case of the coagulated blood represented by the line L42, the phase difference is greater than the phase difference in the case of the non-coagulated blood, and the rate of the increase of the phase lag to the increase of the frequency is also greater than the rate in the case of the non-coagulated blood.

From the experimental results shown in FIG. 5 to FIG. 8, it is possible to distinguish between salt water (sweat) and blood by comparing the amplitude, the phase, or both of the amplitude and the phase in a case of a relatively low frequency and that in a case of a relatively high frequency. Specifically, when a change corresponding to the change in frequency is relatively small, the fluid is determined as salt water or sweat, and when the change is relatively large, the fluid is determined as blood.

For example, as the case of a relatively low frequency, an alternating-current signal of 100 kHz or less is used. For example, as the case of a relatively high frequency, an alternating-current signal of 900 kHz or more is used.

For example, the alternating-current signal output unit 110 inputs an alternating-current signal of 100 kHz as an alternating-current signal in a first frequency to the first conductive body 210 and the second conductive body 220. The alternating-current signal output unit 110 inputs an alternating-current signal of 900 kHz as an alternating-current signal in a second frequency to the first conductive body 210 and the second conductive body 220.

The frequency property acquisition unit 120 measures a phase lag of the impedance between the first conductive body 210 and the second conductive body 220 and the current between the first conductive body 210 and the second conductive body 220 relative to the current output by the alternating-current signal output unit 110 with respect to each of the case of the first frequency and the case of the second frequency.

Then, the detection signal output unit 191 outputs a detection signal, for example, when a measurement value by the frequency property acquisition unit 120 satisfies both of the following conditions (1), (2).

(1) The amplitude of the impedance in the case of the second frequency to the amplitude of the impedance in the case of the first frequency is 97% or less (that is, the amplitude of the impedance in the case of the second frequency is smaller, by 3% or more, than the amplitude of the impedance in the case of the first frequency).

(2) The amplitude of the phase lag in the case of the second frequency to the amplitude of the phase lag in the case of the first frequency is twice or more.

The examples shown in FIG. 7 and FIG. 8 satisfy both of the condition (1) and the condition (2). On the other hand, as shown in the examples of FIG. 5 and FIG. 6, little change in the impedance or the phase lag is observed in the case of salt water or sweat, and it is considered that the condition (1) or the condition (2) is not satisfied.

Accordingly, it is possible to detect an outflow of blood while reducing erroneous detection due to sweat or the like by using the condition (1), the condition (2), or both of the condition (1) and the condition (2).

Further, as shown in FIG. 7 and FIG. 8, the phase change differs between non-coagulated blood and coagulated blood, and therefore, a detection condition can be set such that the detection signal output unit 191 distinguishes between and detect the coagulated blood and the non-coagulated blood.

For example, the fiber sheet 200 may be used for gauze or a bandage applied on a wound after surgery or the like, and the detection signal output unit 191 may detect a state change of the leaked blood coagulating in accordance with the elapse of time. More specifically, the detection signal output unit 191 includes a timer and determines whether or not blood coagulates when it is detected that a predetermined time elapses from when surgery is completed or the like. When it is determined that the blood does not coagulate, the detection device 100 outputs an alarm that prompts confirmation of hemostasis.

When the detection signal output unit 191 detects non-coagulated blood after bleeding from a wound has stopped, the detection device 100 may output an alarm indicating that the wound may open.

Next, with reference to FIG. 9 to FIG. 12, a measurement experiment of a temporal change in a frequency property using a sensor fiber is described.

Figure 9:
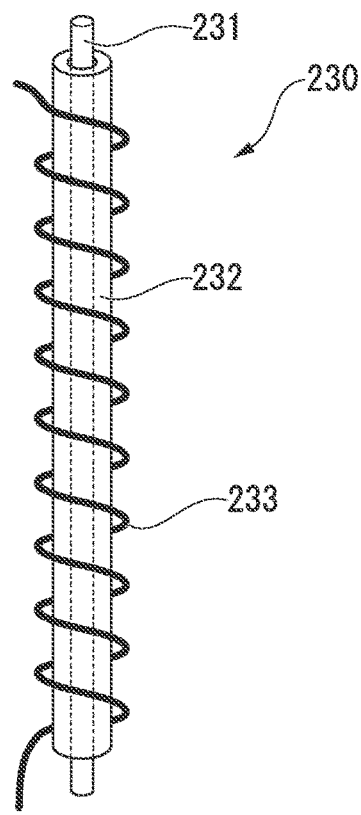
FIG. 9 is a structure view showing a schematic structure of a sensor fiber used in the experiment regarding the embodiment.

FIG. 9 is a structure view showing a schematic structure of a sensor fiber used in the experiment. An insulation cotton 232 is wound around an electrically conductive thread 231, and an electrically conductive thread 233 is wound around the insulation cotton 232 to thereby form a sensor fiber 230 shown in FIG. 9.

Figure 10:
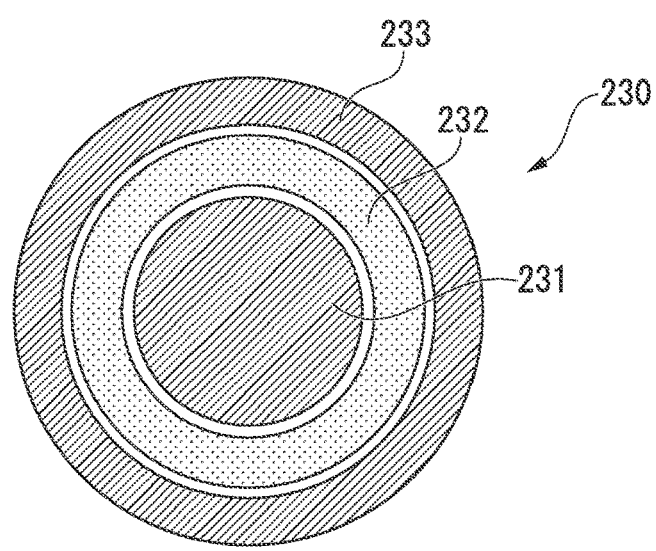
FIG. 10 is an explanatory diagram showing a layer structure of a sensor fiber in the experiment regarding the embodiment.

FIG. 10 is an explanatory diagram showing a layer structure of the sensor fiber 230. FIG. 10 shows a layer structure in a cross-section of the sensor fiber 230. As shown in FIG. 10, the insulation cotton 232 is interposed between the electrically conductive thread 231 and the electrically conductive thread 233. When the insulation cotton 232 absorbs fluid, the frequency property between the electrically conductive thread 231 and the electrically conductive thread 233 is changed.

Figure 11:
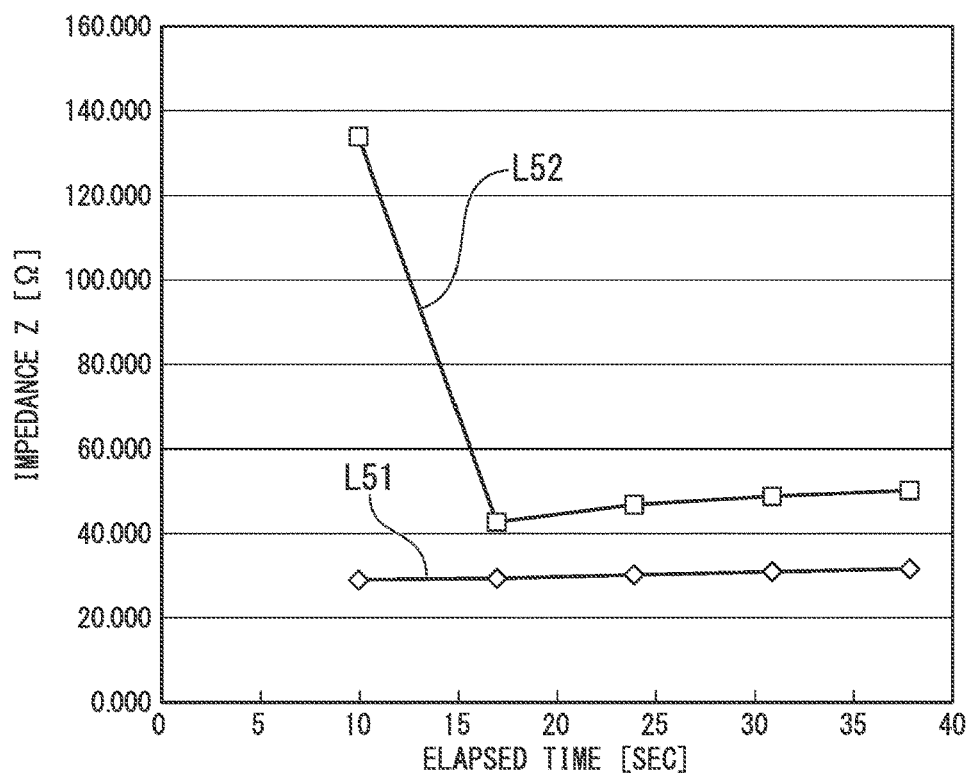
FIG. 11 is a graph showing a temporal change of a measurement value of an amplitude Z of impedance in a state where salt water or blood (swine blood) is dropped on the sensor fiber in the experiment regarding the embodiment.

FIG. 11 is a graph showing a temporal change of a measurement value of an amplitude Z of impedance in a state where salt water or blood (swine blood) is dropped on the sensor fiber. The horizontal axis of the graph shown in FIG. 11 represents elapsed time from the dropping, and the vertical axis represents impedance. A line L51 represents impedance in a state where salt water is dropped, and a line L52 represents impedance in a state where blood is dropped. In the example of FIG. 11, an alternating-current signal of 75 kHz is input to the sensor fiber 230 (electrically conductive threads 231, 233).

The impedance changes little in the case where salt water is dropped represented by the line L51. On the other hand, the impedance once decreases and then increases in the case where blood is dropped represented by the line L52.

Figure 12:
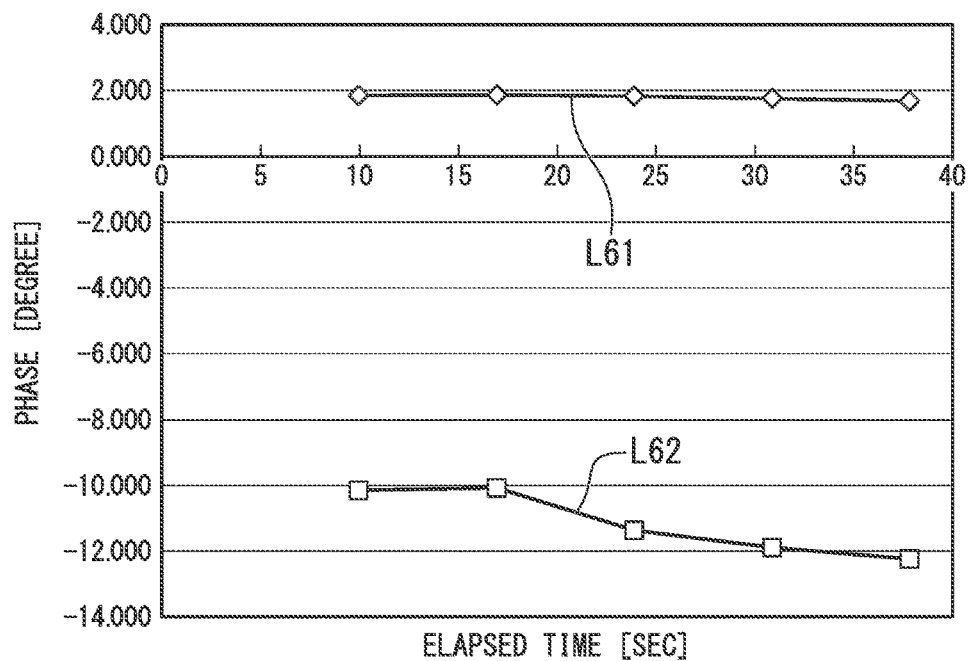
FIG. 12 is a graph showing a temporal change of a measurement value of a phase difference in a state where salt water or blood (swine blood) is dropped on the sensor fiber in the experiment regarding the embodiment.

FIG. 12 is a graph showing a temporal change of a measurement value of a phase difference in a state where salt water or blood (swine blood) is dropped on the sensor fiber. The phase difference here is a phase difference (phase lag) of the alternating-current signal flowing between the electrically conductive threads 231, 233 relative to the phase of the alternating-current signal input to the electrically conductive threads 231, 233.

The horizontal axis of the graph shown in FIG. 12 represents elapsed time from the dropping, and the vertical axis represents a phase difference. A line L61 represents a phase difference in a state where salt water is dropped, and a line L62 represents a phase difference in a state where blood is dropped. In the example of FIG. 11, an alternating-current signal of 1 MHz is input to the sensor fiber 230 (electrically conductive threads 231, 233).

A phase difference in a state where blood is dropped indicated by the line L62 is greater than that in a state where salt water is dropped indicated by the line L61. The phase difference changes little in the case where salt water is dropped. On the other hand, the phase lags in accordance with the elapse of time in the case where blood is dropped.

As shown in FIG. 11 and FIG. 12, the temporal change in the frequency property also differs between salt water and blood. Therefore, as a detection condition of the detection signal output unit 191, a condition with respect to a change in the frequency property according to the elapse of time in addition to or in place of the difference of the frequency property according to the difference of the frequency may be used.

It is considered that the difference of the frequency property between salt water and blood described with reference to FIG. 3 to FIG. 12 is caused by the structure of erythrocytes in blood. More specifically, it is considered that impedance or a phase difference changes depending on the frequency due to a dielectric that comes from an erythrocyte cell membrane. Therefore, the detection device 100 is capable of detecting blood such that blood is distinguished from various fluids including no structure similar to the erythrocyte cell membrane, such as not only sweat but also water or cola. Accordingly, in the detection device 100, it is possible to reduce a possibility in that needle removal is erroneously detected even when a patient spills a beverage such as water or cola.

Next, with reference to FIG. 13 to FIG. 17, an arrangement example of the first conductive body 210 and the second conductive body 220 in the fiber sheet 200 is described. It is possible to variously arrange the first conductive body 210 and the second conductive body 220 in the fiber sheet 200.

Figure 13:
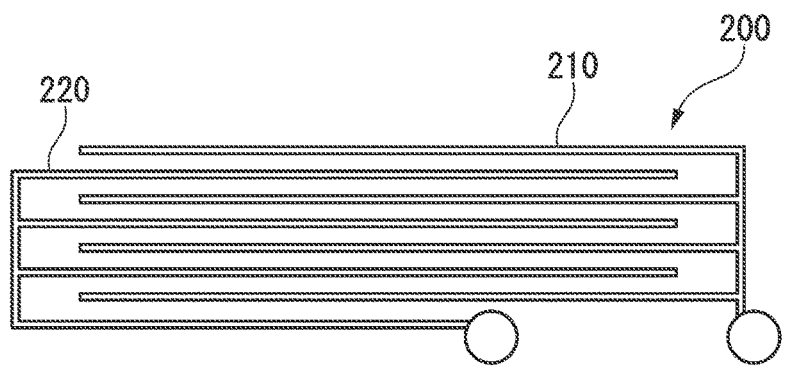
FIG. 13 is an explanatory diagram showing a first example of the arrangement of a first conductive body and a second conductive body in the embodiment.

FIG. 13 is an explanatory diagram showing a first example of the arrangement of the first conductive body 210 and the second conductive body 220. In the arrangement example shown in FIG. 13, the first conductive body 210 and the second conductive body 220 are alternately arranged. When blood is dropped on between the first conductive body 210 and the second conductive body 220, the frequency property between the first conductive body 210 and the second conductive body 220 is changed. Thereby, the detection signal output unit 191 can detect the leakage of blood.

The first conductive body 210 and the second conductive body 220 may be arranged to have some degree of width.

Figure 14:
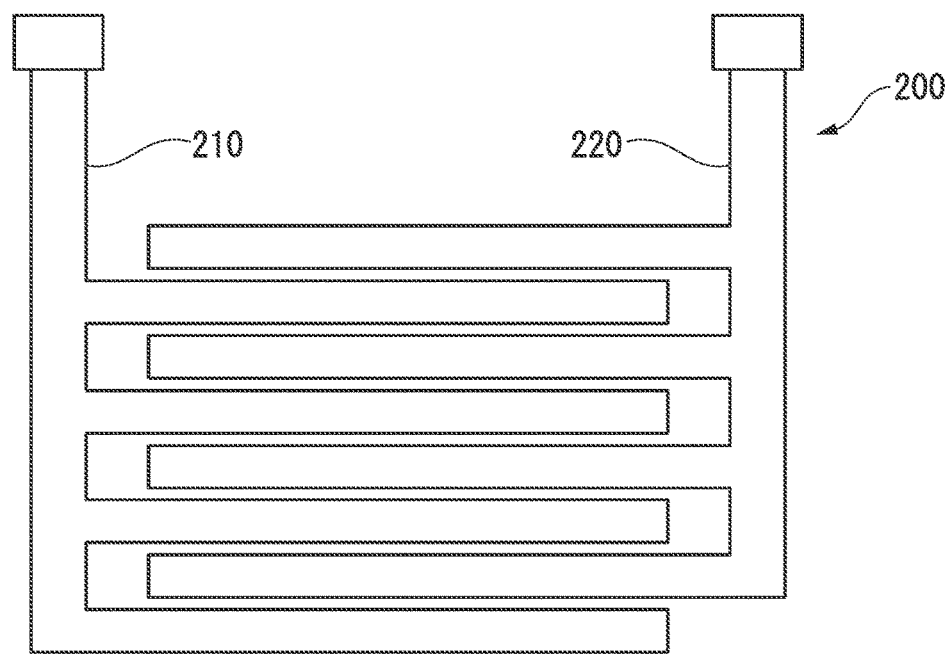
FIG. 14 is an explanatory diagram showing a second example of the arrangement of the first conductive body and the second conductive body in the embodiment.

FIG. 14 is an explanatory diagram showing a second example of the arrangement of the first conductive body 210 and the second conductive body 220. Similarly to the example of FIG. 13, also in the example shown of FIG. 14, the first conductive body 210 and the second conductive body 220 are alternately arranged. However, in the example of FIG. 14, the widths of the first conductive body 210 and the second conductive body 220 are wider than those in the case of FIG. 13. Thereby, the space between the first conductive body 210 and the second conductive body 220 is narrower than that in the case of FIG. 13. As the space between the first conductive body 210 and the second conductive body 220 is narrowed, it is expected that the change of the impedance property when blood is dropped on between the first conductive body 210 and the second conductive body 220 is further increased, and the detection device 100 further easily detects that blood is dropped.

Figure 15:
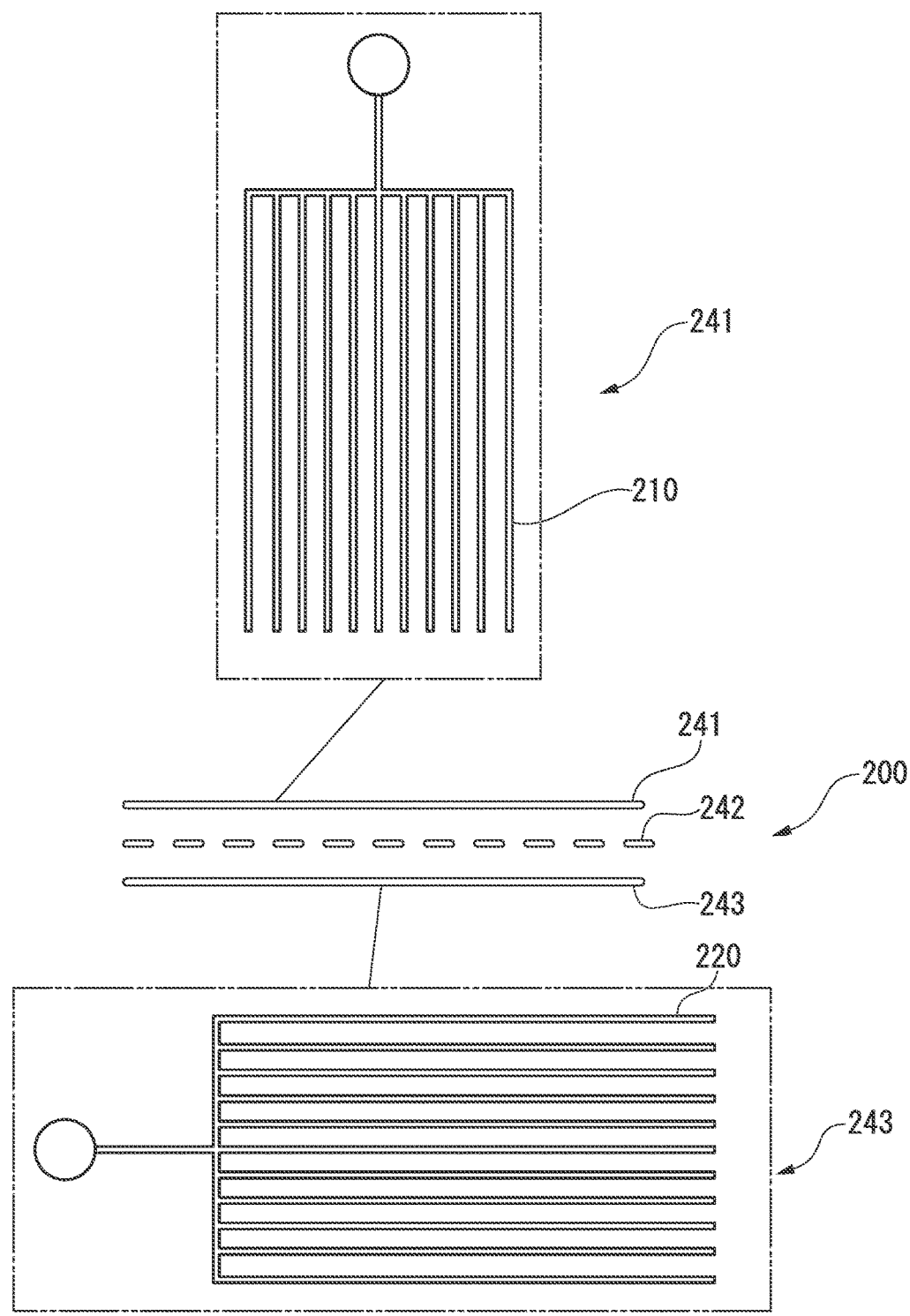
FIG. 15 is an explanatory diagram showing a third example of the arrangement of the first conductive body and the second conductive body in the embodiment.

FIG. 15 is an explanatory diagram showing a third example of the arrangement of the first conductive body 210 and the second conductive body 220. In the arrangement example of FIG. 15, the fiber sheet 200 is formed to have a three-layer structure in which a sheet 242 is interposed between a sheet 241 including the first conductive body 210 and a sheet 243 including the second conductive body 220. The first conductive body 210 and the second conductive body 220 may be arranged to direct to different directions or may be arranged to direct to the same direction.

All of the main body of the sheet 241, the main body of the sheet 243, and the sheet 242 are formed as a sheet having an insulation property and a water absorption property. The sheet 242 is interposed between the first conductive body 210 and the second conductive body 220, and thereby, the first conductive body 210 and the second conductive body 220 are in non-contact with each other. When the sheet 242 absorbs water such as blood, the impedance property between the first conductive body 210 and the second conductive body 220 is changed. Thereby, the detection signal output unit 191 can detect the leakage of blood to the fiber sheet 200.

In the first conductive body 210 and the second conductive body 220, each line may form an independent channel.

Figure 16:
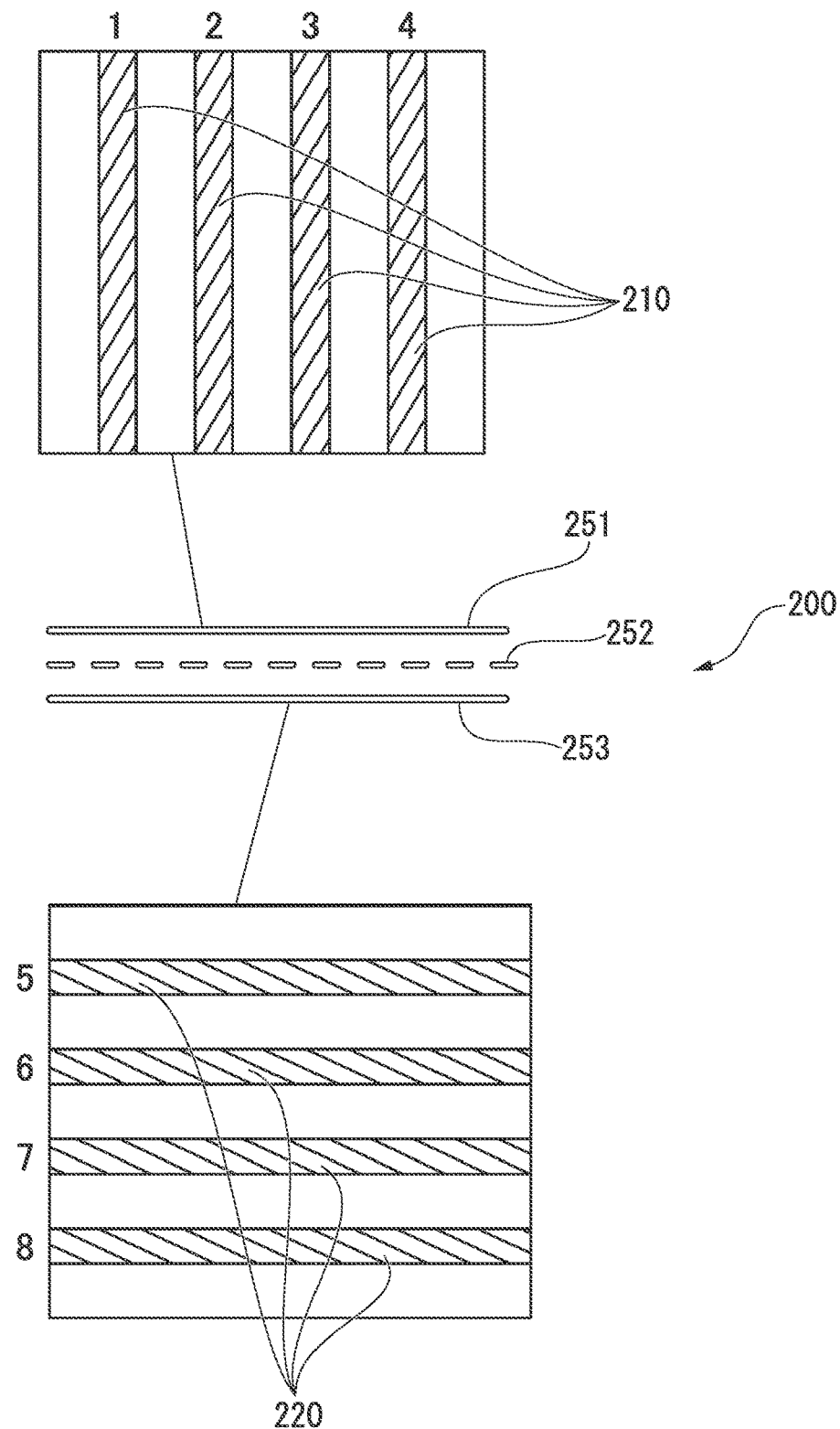
FIG. 16 is an explanatory diagram showing a fourth example of the arrangement of the first conductive body and the second conductive body in the embodiment.

FIG. 16 is an explanatory diagram showing a fourth example of the arrangement of the first conductive body 210 and the second conductive body 220. In the example of FIG. 16, the fiber sheet 200 is formed to have a three-layer structure in which a sheet 252 is interposed between a sheet 251 including the first conductive body 210 and a sheet 253 including the second conductive body 220. The first conductive body 210 and the second conductive body 220 are arranged to direct to different directions. All of the main body of the sheet 251, the main body of the sheet 253, and the sheet 252 are formed as a sheet having an insulation property and a water absorption property. The sheet 252 is interposed between the first conductive body 210 and the second conductive body 220, and thereby, the first conductive body 210 and the second conductive body 220 are in non-contact with each other.

On the other hand, differently from the example of FIG. 15, in the example of FIG. 16, the lines of the first conductive body 210 are not electrically connected to each other, and one of the lines forms each of channels 1 to 4. Further, the lines of the second conductive body 220 are not electrically connected to each other, and one of the lines forms each of channels 5 to 8.

Figure 17:
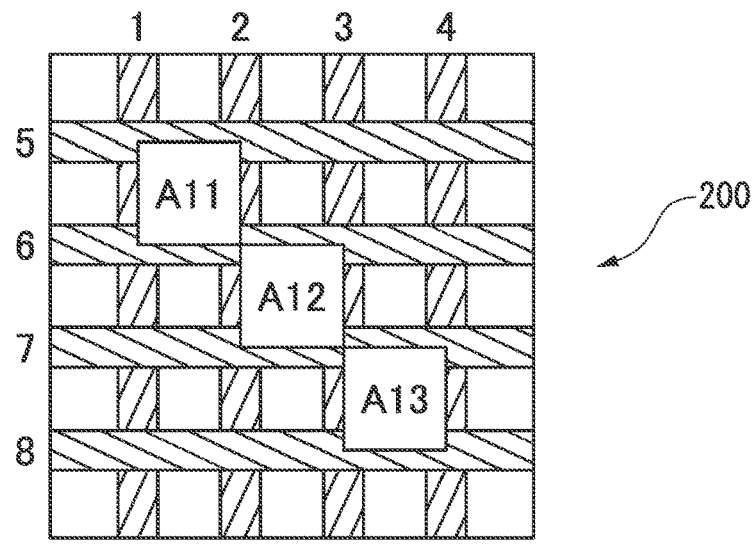
FIG. 17 is an explanatory diagram showing an example of a position relationship between channels of the first conductive body and channels of the second conductive body in the embodiment.

FIG. 17 is an explanatory diagram showing an example of a position relationship between the channels of the first conductive body 210 and the channels of the second conductive body 220. In the example of FIG. 17, the channels of the first conductive body 210 and the channels of the second conductive body 220 are arranged orthogonally to each other. The sheet 252 is interposed between the first conductive body 210 and the second conductive body 220, and thereby, the channels of the first conductive body 210 and the channels of the second conductive body 220 are in non-contact with each other. When fluid sinks into part of the sheet 252, in a channel that corresponds to the position of the part into which the fluid sinks, the frequency property of the first conductive body 210 and the second conductive body 220 is changed. Thereby, the detection signal output unit 191 can detect the leaching position in addition to the presence or absence of the leaching of fluid.

For example, it is assumed that the fiber sheet 200 is used as a carpet, and an apparatus is provided in each of regions A11, A12, A13 on the fiber sheet 200. In this case, if the frequency property between the channel 2 and the channel 5 is changed, it is possible to detect a necessity of protecting the apparatus arranged in the region A11 from a breakdown due to adhesion of fluid or the like. On the other hand, if the frequency property between the channel 3 and the channel 7 is changed, it is possible to detect a necessity of protecting the apparatus arranged in the region A12 and the apparatus arranged in the region A13 from a breakdown due to adhesion of fluid or the like.

In this way, the detection system 1 is applicable to not only the detection of needle removal but also detection of various fluids that change the frequency property between the first conductive body 210 and the second conductive body 220.

When it is unnecessary to distinguish the kinds of fluids, the position at which fluid sinks into the fiber sheet 200 can be detected even by applying a direct current in place of the alternating-current signal to the channel.

For example, in a state where a direct current is applied to the channel 1 and the channel 2, the presence or absence of fluid sinking into the region A11 can be determined by measuring the voltage of each of the channel 5 and the channel 6. In this case, when the electrical conductivity of fluid indicates a sufficiently greater value than the electrical conductivity of air, and a measurement value of a predetermined amplitude or less is obtained with respect to a potential difference between the channel 5 and the channel 6, it is determined that fluid has sunk into the region A11.

At least two conductive bodies may be combined such that the conductive bodies do not come into contact with each other to form a single thread, and the thread may be interwoven into the fiber sheet or be sewed to the fiber sheet.

For example, like the structure shown in FIG. 9 and FIG. 10, the electrically conductive thread 231 is thinly covered by an insulation material having a water absorption property such as the insulation cotton 232 and is further winded by the electrically conductive thread 233 to generate a thread like a coaxial cable. The thread may be further covered by an insulation material having a water absorption property such that the electrically conductive thread 233 does not directly come into contact with the body surface or the like.

Figure 18:
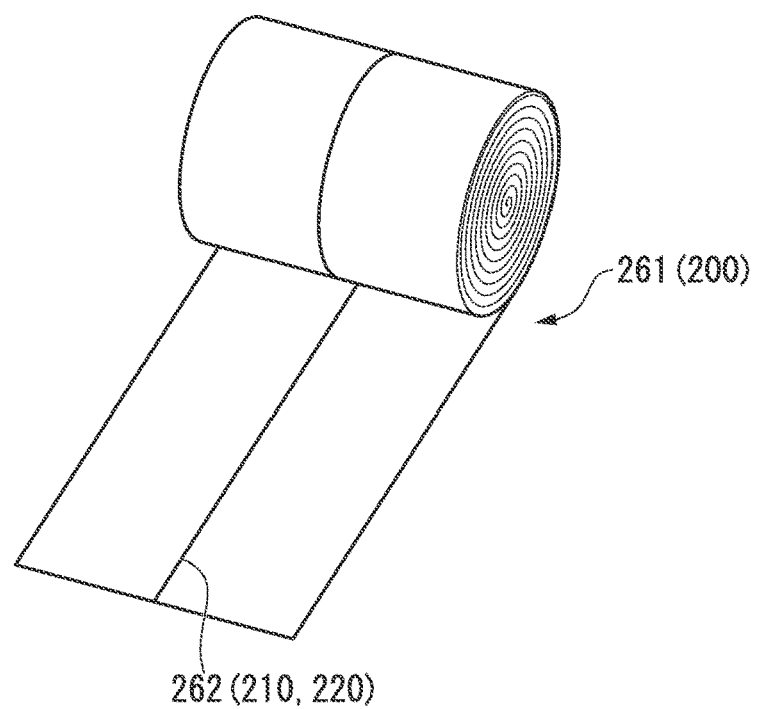
FIG. 18 is an explanatory diagram showing a first example of the arrangement of a thread in which two conductive bodies are combined such that the conductive bodies do not come into contact with each other in the embodiment.

FIG. 18 is an explanatory diagram showing a first example of the arrangement of a thread in which two conductive bodies are combined such that the conductive bodies do not come into contact with each other.

In FIG. 18, a bandage 261 is formed to include a thread 262 that is longitudinally interwoven into a center part of the bandage 261. The thread 262 is formed to include two conductive bodies combined such that the conductive bodies do not come into contact with each other. The bandage 261 corresponds to an example of the fiber sheet 200, and two conductive bodies included in the thread 262 corresponds to an example of the first conductive body 210 and the second conductive body 220.

For example, the bandage 261 is used by winding the bandage 261 around a blood leakage monitor target part such as an arm to which a needle is tapped during artificial dialysis. In the case, the bandage 261 can be cut in an arbitrary length, and by connecting each of the two conductive bodies to the alternating-current signal output unit 110 at one of end parts of the thread 262, the configuration of FIG. 1 can be obtained. Thereby, the detection device 100 can detect the leakage of blood as described above.

Figure 19:
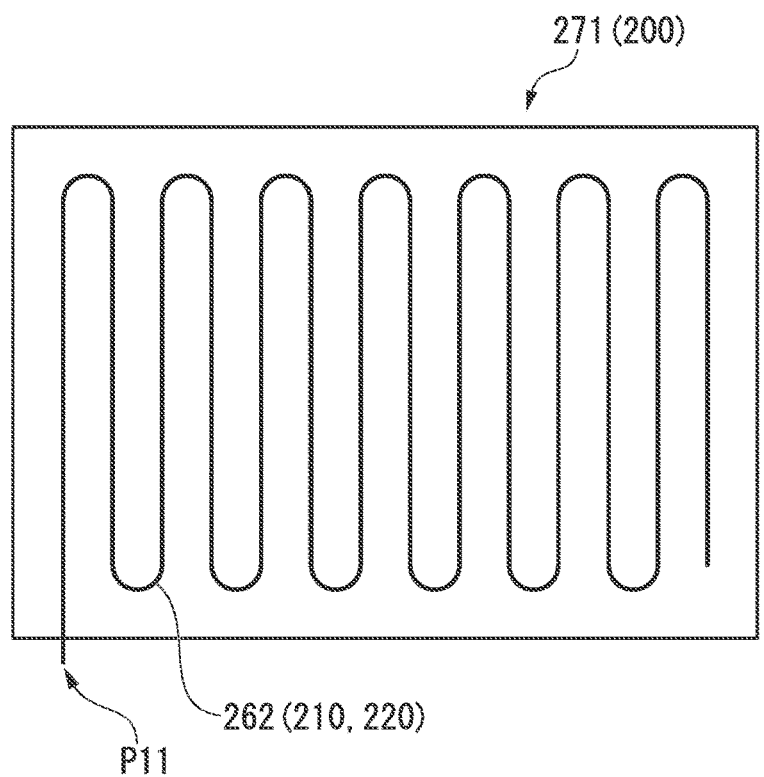
FIG. 19 is an explanatory diagram showing a second example of the arrangement of a thread in which two conductive bodies are combined such that the conductive bodies do not come into contact with each other in the embodiment.

FIG. 19 is an explanatory diagram showing a second example of the arrangement of a thread in which two conductive bodies are combined such that the conductive bodies do not come into contact with each other.

In FIG. 19, a fiber sheet 271 is formed such that a thread 262 is tortuously interwoven into a sheet having an insulation property and a water absorption property. Similarly to the example of FIG. 18, the thread 262 is formed to include two conductive bodies combined such that the conductive bodies do not come into contact with each other. The fiber sheet 271 corresponds to an example of the fiber sheet 200, and two conductive bodies included in the thread 262 corresponds to an example of the first conductive body 210 and the second conductive body 220.

By connecting each of the two conductive bodies to the alternating-current signal output unit 110 at one (for example, a point P11) of end parts of the thread 262, the configuration of FIG. 1 can be obtained. Thereby, the detection device 100 can detect the leakage of blood as described above. Specifically, the thread 262 is tortuously arranged, and thereby, the detection device 100 can detect fluid sinking such as the leakage of blood at a variety of parts of the fiber sheet 271. Thereby, even when a non-stretchable thread 262 is used, the fiber sheet 271 or the bandage 261 can be stretchable.

By using the thread 262 in which two conductive bodies are combined such that the conductive bodies do not come into contact with each other, like the example of FIG. 18 or the example of FIG. 19, a single thread is interwoven into or sewed to a bandage, a fiber sheet, or the like, and the fiber sheet 200 can be formed.

Thereby, it is possible to arrange the two conductive bodies at a relatively narrow interval, and it is possible to enhance the detection accuracy of the detection signal output unit 191 when fluid sinks into the fiber sheet 200.

Further, it is possible to generate the fiber sheet 200 more simply than a case in which each of the two conductive bodies (for example, electrically conductive thread) is interwoven into or sewed to a bandage, a fiber sheet, or the like at a relatively narrow interval and such that the two conductive bodies do not come into contact with each other. Thereby, it is possible to reduce production costs of the fiber sheet 200.

The arrangement of the two conductive bodies included in a single thread is not limited to those shown in the examples of FIG. 9 and FIG. 10.

Figure 20:
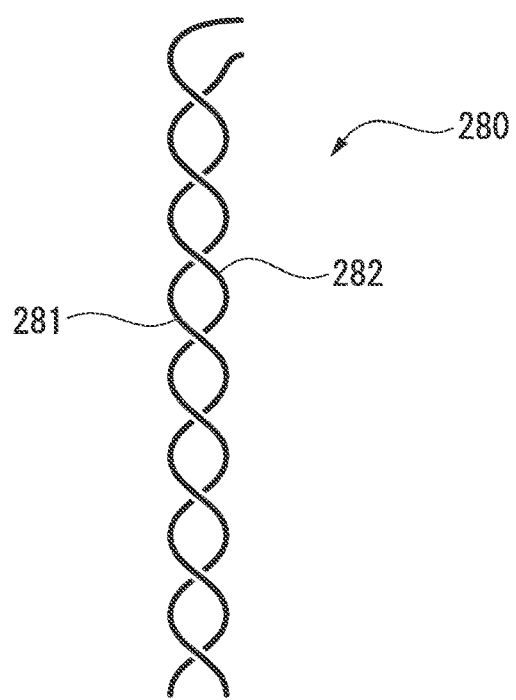
FIG. 20 is an explanatory diagram showing another example of the arrangement of two conductive bodies included in a single thread in the embodiment.

FIG. 20 is an explanatory diagram showing another example of the arrangement of two conductive bodies included in a single thread. In FIG. 20, a thread 280 is formed to include two electrically conductive threads 281, 282 twisted together such that the electrically conductive threads 281, 282 do not come into contact with each other.

For example, the electrically conductive threads 281, 282 are fixed in parallel with each other and in a non-contact manner with each other using a stretchable material such as rubber and are twisted to have an arrangement as shown in FIG. 20. Thereby, the electrically conductive threads 281, 282 can be arranged at a relatively narrow interval, and the thread 280 can be stretchable.

Figure 21:
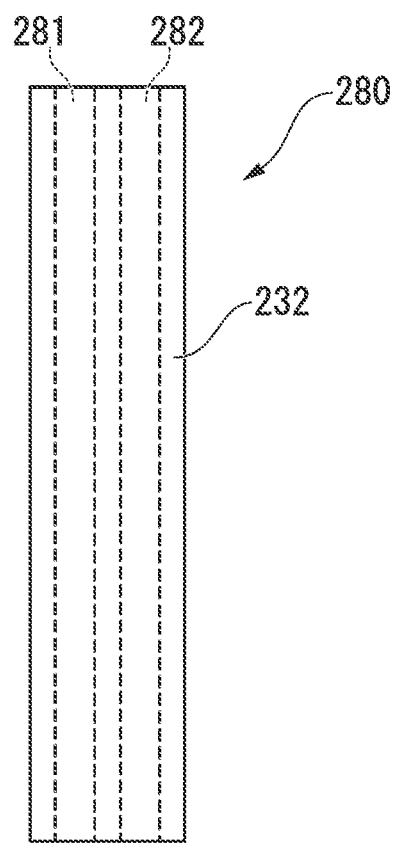
FIG. 21 is an explanatory diagram showing still another example of the arrangement of two conductive bodies included in a single thread in the embodiment.

FIG. 21 is an explanatory diagram showing still another example of the arrangement of two conductive bodies included in a single thread.

Figure 22:
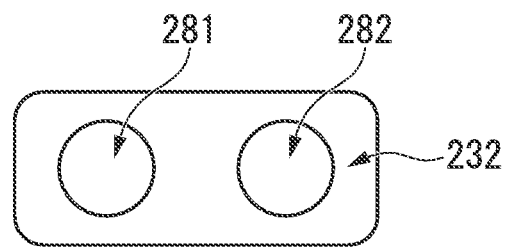
FIG. 22 is an explanatory diagram showing an arrangement example of the two conductive bodies in the cross-section of the thread shown in FIG. 21.

FIG. 22 is an explanatory diagram showing an arrangement example of the two conductive bodies in the cross-section of the thread shown in FIG. 21.

The thread 280 shown in FIG. 21 and FIG. 22 has a structure in which the two electrically conductive threads 281, 282 are arranged in parallel with each other, and the two electrically conductive threads are covered by an insulation material having a water absorption property such as the insulation cotton 232. In the structure, it is unnecessary to twist electrically conductive threads, and in this regard, a thread can be relatively easily produced.

As described above, the frequency property acquisition unit 120 acquires a frequency property when an alternating-current signal is input to at least two conductive bodies provided on a fiber sheet. The detection signal output unit 191 outputs a detection signal when the frequency property acquisition unit 120 acquires a predetermined frequency property.

Thereby, the detection device 100 is capable of detecting adherence of specific fluid such that the specific fluid is distinguished from another fluid according to the difference between frequency properties.

Further, in the detection device 100, a fiber sheet at which at least two conductive bodies (the first conductive body 210 and the second conductive body 220) are provided can be used. For example, a fiber sheet into which a plurality of electrically conductive threads are interwoven can be used as the fiber sheet, and the fiber sheet structure can be simplified. Thereby, production costs of the fiber sheet can be reduced, and the fiber sheet (a part to which fluid adheres) can be disposable.

The frequency property acquisition unit 120 acquires a frequency property when each of an alternating-current signal in a first frequency and an alternating-current signal in a second frequency is input to the at least two conductive bodies (the first conductive body 210 and the second conductive body 220). Then, the detection signal output unit 191 outputs the detection signal when a difference between a frequency property when the alternating-current signal in the first frequency is input to the conductive bodies and a frequency property when the alternating-current signal in the second frequency is input to the conductive bodies is a predetermined difference.

As described above, the rate of the change in the frequency property to the change in the frequency differs between sweat and blood. Therefore, the detection signal output unit 191 can detect blood such that the blood is distinguished from sweat according to the difference between frequency properties in a plurality of frequencies, and it is possible to reduce erroneous detection of needle removal.

In this way, the detection signal output unit 191 can distinguish between and detect specific fluid and another fluid according to the difference between frequency properties in a plurality of frequencies.

The fiber sheet 200 includes a thread (the thread 262 or the thread 280) including at least two conductive bodies 210, 220 which are combined such that the conductive bodies do not come into contact with each other.

Thereby, it is possible to arrange the two conductive bodies 210, 220 at a relatively narrow interval, and it is possible to enhance the detection accuracy of the detection signal output unit 191 when fluid sinks into the fiber sheet 200.

Further, it is possible to generate the fiber sheet 200 more simply than a case in which each of the two conductive bodies 210, 220 is interwoven into or sewed to a bandage, a fiber sheet, or the like at a relatively narrow interval and such that the two conductive bodies do not come into contact with each other. Thereby, it is possible to reduce production costs of the fiber sheet 200.

A program for realizing the function of the detection signal output unit 191 may be recorded in a computer-readable recording medium, and the program recorded in the recording medium may be read into and executed on a computer system to thereby perform the process of each unit. It is assumed that the term "computer system" used herein includes an OS or hardware such as peripherals.

It is also assumed that the term "computer system" includes a homepage providing environment (or a display environment) when utilizing a WWW system.

The term "computer-readable recording medium" refers to a portable medium such as a flexible disk, a magneto-optical disk, a ROM, or a CD-ROM or a storage device such as a hard disk embedded in the computer system. It is also assumed that the term "computer-readable recording medium" includes a medium which dynamically holds a program for a short period of time like a communication line when a program is transmitted through a network such as the Internet or a communication line such as a telephone line and a medium which holds a program for a given time like a volatile memory in the computer system which becomes a server or a client in the case. The program may be a program which can realize part of the above-described functions or may be a program which can realize the above-described functions by a combination with a program already recorded in the computer system.

Although an embodiment of the invention has been described in detail referring to the drawings, a specific configuration is not limited to the embodiment and design changes and the like can be made without departing from the scope of the invention.

DESCRIPTION OF THE REFERENCE SYMBOLS

1: detection system
100: detection device
110: alternating-current signal output unit
120: frequency property acquisition unit
130: alarm output unit
180: storage unit
181: detection condition storage unit
190: control unit
191: detection signal output unit
200, 271: fiber sheet
210: first conductive body
220: second conductive body
230: sensor fiber
231, 233, 281, 282: electrically conductive thread
232: insulation cotton
241, 242, 243, 251, 252, 253: sheet
261: bandage
262, 280: thread

The invention claimed is:

1. A detection system for detecting a specific fluid comprising:
a first conductive body;
a second conductive body;
an intermediate material adapted to absorb fluid, at least a part of the intermediate material being disposed between the first conductive body and the second conductive body;
a frequency property acquisition unit that acquires a frequency property in a case where an alternating-current signal is input to the first conductive body and the second conductive body; and
a detection signal output unit that outputs a detection signal indicative of detection of the specific fluid absorbed in the intermediate material between the first conductive body and the second conductive body, based on a difference between the frequency property acquired by the frequency property acquisition unit in a case where the alternating-current signal in a first frequency is input to the first conductive body and the second conductive body and the frequency property acquired by the frequency property acquisition unit in a case where the alternating-current signal in a second frequency different from the first frequency is input to the first conductive body and the second conductive body.

2. The detection device according to claim 1, wherein the frequency property acquired by the frequency property acquisition unit is a phase lag of the alternating-current signal flowing between the first conductive body and the second conductive body relative to the alternating-current signal input to the first conductive body and the second conductive body.

3. The detection system according to claim 1, wherein the specific fluid to be detected is blood.

4. The detection system according to claim 1, further comprising a fiber sheet including a thread including the first conductive body and the second conductive body which are combined such that the first and second conductive bodies do not come into contact with each other.

5. The detection system according to claim 4, wherein the thread further includes the intermediate material being an insulation material, the first conductive body being a first electrically conductive thread, the second conductive body being a second electrically conductive thread, and the first electrically conductive thread is covered by the insulation material and is further winded by the second conductive body.

6. The detection system according to claim 1, wherein the first and second conductive bodies are twisted together such that the first and second conductive bodies do not come into contact with each other.

7. A detection method for detecting a specific fluid, using a detection system including a first conductive body, a second conductive body and an intermediate material, the detection method comprising:

by way of the detection system, acquiring a frequency property in a case where an alternating-current signal is input to the first conductive body and the second conductive body; and by way of the detection system, outputting a detection signal indicative of detection of the specific fluid absorbed in the intermediate material between the first conductive body and the second conductive body, based on a difference between the frequency property in a case where the alternating-current signal in a first frequency is input to the first conductive body and the second conductive body and the frequency property in a case where the alternating-current signal in a second frequency different from the first frequency is input to the first conductive body and the second conductive body.

8. A non-transitory computer-readable storage medium that stores a program that allows a computer to execute functions of a detection system including a first conductive body, a second conductive body and an intermediate material so that the computer executes the steps comprising:

acquiring a frequency property in a case where an alternating-current signal is input to the first conductive body and the second conductive body; and outputting a detection signal indicative of detection of the specific fluid absorbed in the intermediate material between the first conductive body and the second conductive body, based on a difference between the frequency property in a case where the alternating-current signal in a first frequency is input to the first conductive body and the second conductive body and the frequency property in a case where the alternating-current signal in a second frequency different from the first frequency is input to the first conductive body and the second conductive body.

9. A detection system for detecting a specific fluid comprising:

a memory;

a first conductive body;

a second conductive body;

an intermediate material adapted to absorb fluid, at least a part of the intermediate material being disposed between the first conductive body and the second conductive body;

a frequency property acquirer that acquires a frequency property in a case where an alternating-current signal is input to the first conductive body and the second conductive body; and a processor, in communication with the acquirer and the memory, configured to output a detection signal indicative of detection of the specific fluid absorbed in the intermediate material between the first conductive body and the second conductive body, based on a difference between the frequency property acquired by the frequency property acquirer in a case where the alternating-current signal in a first frequency is input to the first conductive body and the second conductive body and the frequency property acquired by the frequency property acquirer in a case where the alternating-current signal in a second frequency different from the first frequency is input to the first conductive body and the second conductive body.

10. A detection system for detecting a specific fluid comprising:

a memory;

a sensor fiber including a first conductive body, a second conductive body, an intermediate material adapted to absorb fluid, the intermediate material covering the first conductive body, the insulation material being winded by the second conductive body so that the sensor fiber is in the form of a thread like a coaxial cable;

a frequency property acquirer that acquires a frequency property in a case where an alternating-current signal is input to the first conductive body and the second conductive body; and a processor, in communication with the acquirer and the memory, configured to output a detection signal indicative of detection of the specific fluid between the first conductive body and the second conductive body, based on a difference between the frequency property acquired by the frequency property acquirer in a case where the alternating-current signal in a first frequency is input to the first conductive body and the second conductive body and the frequency property acquired by the frequency property acquirer in a case where the alternating-current signal in a second frequency different from the first frequency is input to the first conductive body and the second conductive body.

* * * * *